United States Patent
Leach

(10) Patent No.: US 10,232,104 B2
(45) Date of Patent: Mar. 19, 2019

(54) CELL FILTER SEPARATION SYSTEM

(71) Applicant: Biomet Manufacturing, LLC, Warsaw, IN (US)

(72) Inventor: Michael D. Leach, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 228 days.

(21) Appl. No.: 15/119,205

(22) PCT Filed: Feb. 25, 2015

(86) PCT No.: PCT/US2015/017513
§ 371 (c)(1),
(2) Date: Aug. 16, 2016

(87) PCT Pub. No.: WO2015/130778
PCT Pub. Date: Sep. 3, 2015

(65) Prior Publication Data
US 2017/0007757 A1    Jan. 12, 2017

Related U.S. Application Data

(60) Provisional application No. 61/944,333, filed on Feb. 25, 2014.

(51) Int. Cl.
*A61M 1/02* (2006.01)
*A61M 1/36* (2006.01)

(52) U.S. Cl.
CPC ........ *A61M 1/3692* (2014.02); *A61M 1/0281* (2013.01); *A61M 2202/0429* (2013.01)

(58) Field of Classification Search
CPC ............. A61M 1/0281; A61M 1/3692; A61M 2202/0429
USPC .................................................. 210/650, 651
See application file for complete search history.

(56) References Cited

U.S. PATENT DOCUMENTS

| | | | | |
|---|---|---|---|---|
| 4,919,817 A | * | 4/1990 | Schoendorfer | A61M 1/34 210/321.68 |
| 5,282,982 A | * | 2/1994 | Wells | A61M 1/02 210/723 |
| 6,491,819 B2 | * | 12/2002 | Prince | B01D 39/1692 210/321.67 |
| 9,895,482 B2 | * | 2/2018 | Kusters | A61M 1/0272 |
| 2013/0334139 A1 | * | 12/2013 | Blickhan | A61M 1/0272 210/650 |

(Continued)

FOREIGN PATENT DOCUMENTS

WO    WO-8504112 A1    9/1985
WO    WO-8801193 A1    2/1988

(Continued)

OTHER PUBLICATIONS

"European Application Serial No. 15708099.5, Response filed Jan. 29, 2018 to Communication Pursuant to Article 94(3) EPC dated Sep. 21, 2017", 15 pgs.
"International Application Serial No. PCT/US2015/017513, International Preliminary Report on Patentability dated Sep. 9, 2016", 15 pgs.
"European Application Serial No. 15708099.5, Communication Pursuant to Article 94(3) EPC dated Sep. 21, 2017", 6 pgs.
"Serial No. 15708099.5, Response filed Apr. 24, 2017 to European Office Action dated Oct. 13, 2017", 17 pgs.

(Continued)

*Primary Examiner* — Ellen M McAvoy
(74) *Attorney, Agent, or Firm* — Schwegman Lundberg & Woessner, P.A.

(57) ABSTRACT

Separation of a wash liquid from red blood cells is disclosed using a filter separation and pressure differential system. The filter may include a membrane filter.

11 Claims, 1 Drawing Sheet

(56) References Cited

U.S. PATENT DOCUMENTS

| | | | | |
|---|---|---|---|---|
| 2015/0166957 A1* | 6/2015 | Kusters | ............... | A61M 1/3496 |
| | | | | 435/2 |
| 2016/0106353 A1* | 4/2016 | Schuetz | .............. | A61M 1/0281 |
| | | | | 210/321.6 |
| 2016/0144098 A1* | 5/2016 | Radwanski | ......... | A61M 1/3692 |
| | | | | 210/651 |
| 2016/0235905 A1* | 8/2016 | Matsuura | ............ | A61M 1/0281 |
| 2016/0243293 A1* | 8/2016 | Matsuura | ............ | A61M 1/0281 |

FOREIGN PATENT DOCUMENTS

| | | |
|---|---|---|
| WO | WO-0023140 A1 | 4/2000 |
| WO | WO-03074077 A1 | 9/2003 |
| WO | WO-2012125457 A1 | 9/2012 |
| WO | WO-2013043433 A2 | 3/2013 |
| WO | WO-2015130778 A1 | 9/2015 |

OTHER PUBLICATIONS

"International Application Serial No. PCT/US2015/017513, International Search Report dated Jun. 1, 2015", 5 pgs.

"International Application Serial No. PCT/US2015/017513, Written Opinion dated Jun. 1, 2015", 13 pgs.

"European Application Serial No. 15708099.5, Summons to Attend Oral Proceedings mailed Jul. 26, 2018", 15 pgs.

Fenwal, "ADSOL Safety Data Sheet", (May 11, 2013), 1-5.

"European Application No. 15708099.5, Response filed Jan. 4, 2019 to Summons to Attend Oral Proceedings dated Jul. 26, 2018", 39 pgs.

\* cited by examiner

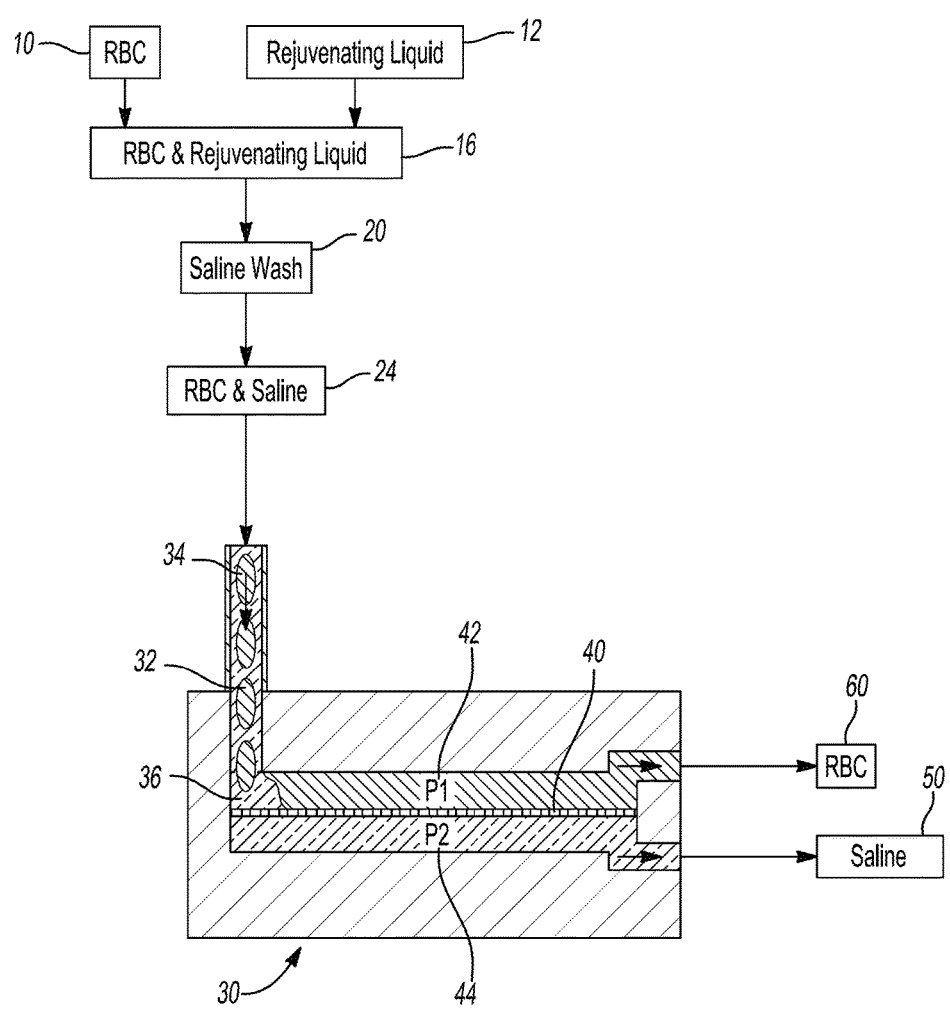

CELL FILTER SEPARATION SYSTEM

PRIORITY APPLICATION

This application is a U.S. National Stage Application under 35 U.S.C. 371 from International Application No. PCT/US2015/017513, filed Feb. 25, 2015, published as WO 2015/130778 on Sep. 3, 2015, which application claims the benefit of priority to U.S. Provisional Patent Application Serial No. 61/944,333, filed Feb. 25, 2014, the contents of which are incorporated by reference in their entireties.

FIELD

The subject disclosure relates to separation, and particularly to the separation of cells from a carrier liquid.

BACKGROUND

This section provides background information related to the present disclosure which is not necessarily prior art.

In various procedures a cell population may be suspended or held in a liquid carrier. For example, whole blood or red blood cells can be held in a liquid carrier or washed in a liquid. For example, separated red blood cells can be mixed with Rejuvesol® solutions for use in the extracorporeal rejuvenation of red blood cells that can assist in maintaining or rejuvenating cells after a period of storage. The Rejuvesol® solutions, however, may be selectively removed from the red blood cells prior to introduction of the red blood cells into a patient. The removal of the Rejuvesol® solutions can be performed with a selected biocompatible solution, such as sterile saline. The saline, however, may dilute the red blood cells and it may be desirable to remove the saline from the red blood cells population prior to introduction to the patient.

SUMMARY

This section provides a general summary of the disclosure, and is not a comprehensive disclosure of its full scope or all of its features.

Separation of saline from red blood cells may be performed with a filter separation and pressure differential system. The filter may include a membrane filter. The membrane filter, discussed further herein, may be included in a separation system.

In various embodiments, an introduction of red blood cells carried in a saline liquid can be introduced to a separation system with a filter membrane. In the separation system the carrier liquid may pass through the filter membrane. The red blood cells may not pass or easily pass through the filter membrane and, therefore, are separated from at least a portion of the saline carrier liquid.

It is further understood that a separation system need not be used only to separate red blood cells from saline. Rather, red blood cells may be separated from any selected fluid, such as directly from the Rejuvesol® rejuvenating liquid directly. Further, any appropriate cellular material can be removed from any selected liquid carrier for various purposes, such as removing stem cells from a liquid carrier or storage medium, or other selected materials. Further, biological or animal cells need not be separated from a carrier liquid, but rather any solid or potential solid particle may be separated from a carrier liquid. For example, a particle has a size on a dimension similar to that of the red blood cell or generally having an average width dimension in a range of about 5 μm to about 10 μm may be separated from a carrier or suspension liquid.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

The FIGURE is a schematic illustration of a cell separation system having a membrane filter.

DETAILED DESCRIPTION

Example embodiments will now be described more fully with reference to the accompanying drawings.

In various procedures, red blood cells (RBC) may be introduced to a patient, such as a human patient or subject, for various purposes. For example, blood loss may occur due to an injury or surgical procedure. The red blood cells may be collected and stored for a period of time prior to use, such as prior to a surgical procedure. The red blood cells, therefore, may have sub-optimal or sub-normal oxygen or energy carrying capabilities due to degradation of adenine-tri-phosphate (ATP) and other selected energy carrying molecules. Various materials, such as Rejuvesol® solutions can be used to assist in rejuvenating and raising levels of selected compounds in a red blood cell to optimal or naturally occurring levels. It can be selected to remove the Rejuvesol® solutions, however, prior to introduction of the red blood cells to a patient.

The following disclosure is generally directed to removal or separation of red blood cells from the carrier liquid. It is understood, however, that separation of any appropriate cells may be made from any appropriate or selected liquid carrier. Further, separation of a particle that is similar in size to a cell, such as a particle having a size range of about 5 μm to about 10 μm can be separated from a carrier liquid. Accordingly, it is understood, that the following disclosure is not related only to a medical or anatomical procedure.

With reference to the FIGURE a red blood cell population 10 can be mixed with a selected material, such as Rejuvesol® solution 12 in a mixing structure or system to form a mixture of red blood cells and the solution 16. After a selected rejuvenating period in a mixing or bath condition, as generally understood in the art, the rejuvenating liquid can be washed from the RBCs with a washing liquid, such as saline. Other appropriate washing liquids may also be used and the subject disclosure is understood to not be limited to a saline washing liquid.

According to various embodiments, the RBC and rejuvenating liquid mixture 16 can be washed with saline in a saline washing system 20 according to a selected wash procedure. The selected wash procedure may proceed according to generally known washing techniques including parameters relative to time, agitation force, volume, etc. Washing the rejuvenating liquid from the RBCs can be performed in generally known techniques, such as with agitation or sonic mixing. This can form an RBC and saline mixture 24 where the RBCs have been rejuvenated with the rejuvenating liquid and are now suspended or carried in a volume of saline. It is understood, however, that the RBC and saline mixture 24 may include a small amount of the rejuvenating solution as the wash may not be 100% efficient.

The RBC and saline mixture can be introduced to a separating system 30 through a mixture input 32. As illustrated in the FIGURE, RBCs 34 can be carried in the saline material 36 into the separating system 30. It is understood, however, that the RBCs are generally understood to be large particles relative to the size of the saline carrying fluid. Accordingly, the RBCs may be separated from the saline material using a membrane 40 having a selected pour size such as about 0.1 µm to about 10 µm, including about 1 µm to about 10 µm, and further including about 2 µm to about 8 µm. It can be selected to have a pore size of the membrane to be smaller than a RBC size of a majority of the population of the RBCs. Thus, a majority of the population of the RBCs in the mixture 24 will be retained.

In the separation system, a pressure differential between a RBC flow side 42 and a saline flow side 44 may be maintained or selected to achieve an appropriate separation of the RBCs 34 from the saline carrier 36. The pressure selected can include a pressure P1 in the RBC flow side 42 that is higher than a pressure P2 in the saline flow side 44 to force or cause a flow of the saline to the saline flow side 44. The saline flow side 44 may include a higher concentration of saline relative to the RBC flow side 42, at least downstream from an input, thus a higher pressure in the RBC flow side 42 may be needed to cause a selected amount of separation. The pressure may be maintained using generally known flow pressure regulation systems. Generally, the pressure differential generates a reverse osmosis action such that the saline flows or moves through the member 40 to the saline flow side 44 of the membrane and away from the RBC flow side 42. Thus, the saline is removed from the mixture 24.

Certain systems are known that allow for control (e.g. selection of pressure) and maintaining selected pressures, such as the pressures P1 and P2 in a flow system. For example, the SEP01, SEP10, or SEP200 Liquid-Liquid Separators sold by Zaiput Flow Technologies include integrated pressure control systems to control pressure within a separation system. It is understood that external pressure regulation systems may also be used to regulate pressure in a flow separation system. Further, input side and/or output side pressure control systems may be used to regulate pressure in the separation system 30.

Further, the membrane 40 can be selected of a material that is substantially saline-phylic by the saline carrier fluid. This attribute of the membrane 40 may enhance or maximize the separation of the saline liquid from the RBCs. It can be further selected that the membrane is substantially RBC-phobic. Thus, the membrane 40 can assist in repelling the RBCs.

In the separation system 30, due to the flow of the saline liquid 36 and the RBCs 34 at a selected flow rate and pressure relative to the membrane 40, the saline liquid 36 can pass through the membrane 40 and follow a saline route side to a saline collector area 50. The saline route or side 44 is separate from the RBC flow path 42 to allow for collection of the RBCs in a RBC collector 60. Thus, the wash solution can be removed from the RBCs to allow for collection of a high concentration of RBCs in the RBC collection area 60. Generally, the RBCs collected in the RBC collection volume 60 can be at a concentration of about 2× to about 10× greater than the introduced RBC concentration from the RBC and saline mixture volume 24.

Accordingly, the RBCs can be collected in the RBC collection volume 60 in a substantially continuous flow through the separation system 30 from the mixture volume 24 of the RBC and wash solution, which can include saline. It is further understood that the flow through the separation 30 can be selected at a flow rate to achieve a selected separation concentration of the RBCs in the collector volume 60. Accordingly, a flow rate can be selected for a concentration that is not equal to a maximum concentration volume if a higher flow rate is selected, such as for immediacy of production of RBCs. Nevertheless, RBCs can be collected in the RBC collection volume 60 substantially separated from a wash or carrier liquid, such as the saline wash 20, to allow for introduction of a high concentration of RBCs into a patient.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of removing a wash liquid from a mixture, the method comprising:
   - forming a mixture at least by mixing red blood cells with a wash liquid including saline;
   - selecting a filter membrane that is substantially saline-phylic and red blood cell-phobic;
   - flowing the mixture over a first side of the filter membrane; and
   - forcing the wash liquid to a second side of the filter member opposite the first side;
   - wherein at least a portion of the wash liquid including saline is separated across the filter membrane from the mixture.

2. The method of claim 1, further comprising collecting at least the red blood cells from the first side of the filter member.

3. The method of claim 2,
   - wherein flowing the mixture over the first side of the filter membrane includes a substantially continuous flow over the first side of the filter membrane;
   - wherein the collecting at least the red blood cells from the first side of the filter member includes collecting an outflow from the first side of the membrane.

4. The method of claim 1, further comprising selecting a pore size of the filter membrane to be smaller than a particle size of a majority of the population of the red blood cells.

5. The method of claim 1, further comprising fixing the filter membrane to form a first side outflow between a mixture input and a red blood cells outlet and a second side outflow separate from the first side outflow between the mixture input and a saline outlet.

6. The method of claim 5, further comprising controlling a pressure differential between the red blood cells outlet and the saline outlet to at least assist in the forcing the wash liquid to the second side of the filter member opposite the first side.

7. A system to separate at least a red blood cell portion of a mixture from the remainder of the mixture, the system comprising:
- a system having a mixture input and at least a red blood cell (RBC) outlet and a saline outlet;
- a membrane having a selected pore size separating the RBC outlet and the saline outlet, the membrane being substantially saline-phylic and red blood cell-phobic; and
- a pressure control system to cause separation of the RBC from the saline across the membrane.

8. The system of claim 7, wherein the RBC has a large particle size relative to a size of the saline.

9. The system of claim 8, wherein the membrane includes a pore size to be smaller than a particle size of a majority of the population of the RBC.

10. The system of claim 7, wherein the membrane is fixed within the system to cause a RBC flow side between the mixture input and the RBC outlet and a saline flow side separate from the RBC flow side between the mixture input and the saline outlet.

11. The system of claim 10, wherein the pressure control system causes a pressure differential between the RBC flow side and the saline flow side.

* * * * *